(12) United States Patent
Sutton (10) Patent No.: US 11,724,103 B1
(45) Date of Patent: Aug. 15, 2023

(54) APPARATUS AND METHOD FOR ANCHORING A LEAD OF A DORSAL ROOT GANGLION STIMULATION SYSTEM

(71) Applicant: Brandon Sutton, Louisville, KY (US)

(72) Inventor: Brandon Sutton, Louisville, KY (US)

(*) Notice: Subject to any disclaimer, the term of this patent is extended or adjusted under 35 U.S.C. 154(b) by 170 days.

(21) Appl. No.: 17/518,977

(22) Filed: Nov. 4, 2021

Related U.S. Application Data (60) Provisional application No. 63/110,585, filed on Nov. 6, 2020.

(51) Int. Cl.
  *A61N 1/05* (2006.01)
  *A61N 1/36* (2006.01)

(52) U.S. Cl.
  CPC ....... *A61N 1/0558* (2013.01); *A61N 1/36062* (2017.08)

(58) Field of Classification Search
  CPC .............. A61N 1/0558; A61N 1/36062; A61N 1/0593; A61N 1/0551; A61N 1/057; A61N 1/0573; A61N 2001/058; A61N 2001/059; A61N 1/37518
  See application file for complete search history.

(56) References Cited

U.S. PATENT DOCUMENTS

| | | | |
|---|---|---|---|
| 8,311,643 B2 | 11/2012 | North | |
| 9,199,074 B2 | 12/2015 | Pianca | |
| 10,159,838 B2 | 12/2018 | Kim et al. | |
| 2013/0317587 A1 | 11/2013 | Barker | |

OTHER PUBLICATIONS

Abbott Medical, Proclaim DRG Implantable Pulse Generator Model 3664, Clinician's Manual, 2018.

*Primary Examiner* — Paula J Stice
(74) *Attorney, Agent, or Firm* — Stites & Harbison, PLLC; David W. Nagle, Jr.

(57) ABSTRACT

In an apparatus and method for anchoring a lead of a dorsal root ganglion stimulation system, the apparatus comprises: a grommet carrying one or more sutures, wherein the grommet includes a ring with multiple teeth that extend radially inward from the ring; and a deployment device configured to receive and secure the grommet at its distal end. A plunger of the deployment device transitions between a stored position and a deployed position relative to a barrel. When the plunger is transitioned to the deployed position, the plunger contacts and bends the multiple teeth of the grommet relative to the ring, extending the multiple teeth outward into adjacent fascia, thus anchoring the grommet to the fascia, such that the one or more sutures are available for anchoring a selected lead of the dorsal root ganglion stimulation system to the fascia.

11 Claims, 11 Drawing Sheets

APPARATUS AND METHOD FOR ANCHORING A LEAD OF A DORSAL ROOT GANGLION STIMULATION SYSTEM

CROSS-REFERENCE TO RELATED APPLICATIONS

The present application claims priority to U.S. Patent Application Ser. No. 63/110,585 filed on Nov. 6, 2020, the entire disclosure of which is incorporated herein by reference.

BACKGROUND OF THE INVENTION

A dorsal root ganglion is a cluster of nerves disposed along a dorsal root of a spinal nerve, in proximity to the spinal cord and the vertebral column.

In February 2016, the U.S. Food and Drug Administration approved a treatment for patients with complex regional pain syndrome (CRPS I and II) in the lower extremities via electrical stimulation of the dorsal root ganglion. Dorsal root ganglion (DRG) stimulation is an outpatient neuromodulation therapy, similar to traditional spinal cord (SCS) stimulation. DRG stimulation is described, for example, in U.S. Pat. Nos. 10,159,838, 9,199,074, and U.S. Patent Application Publication No. 2013/0317587.

Figure 1:
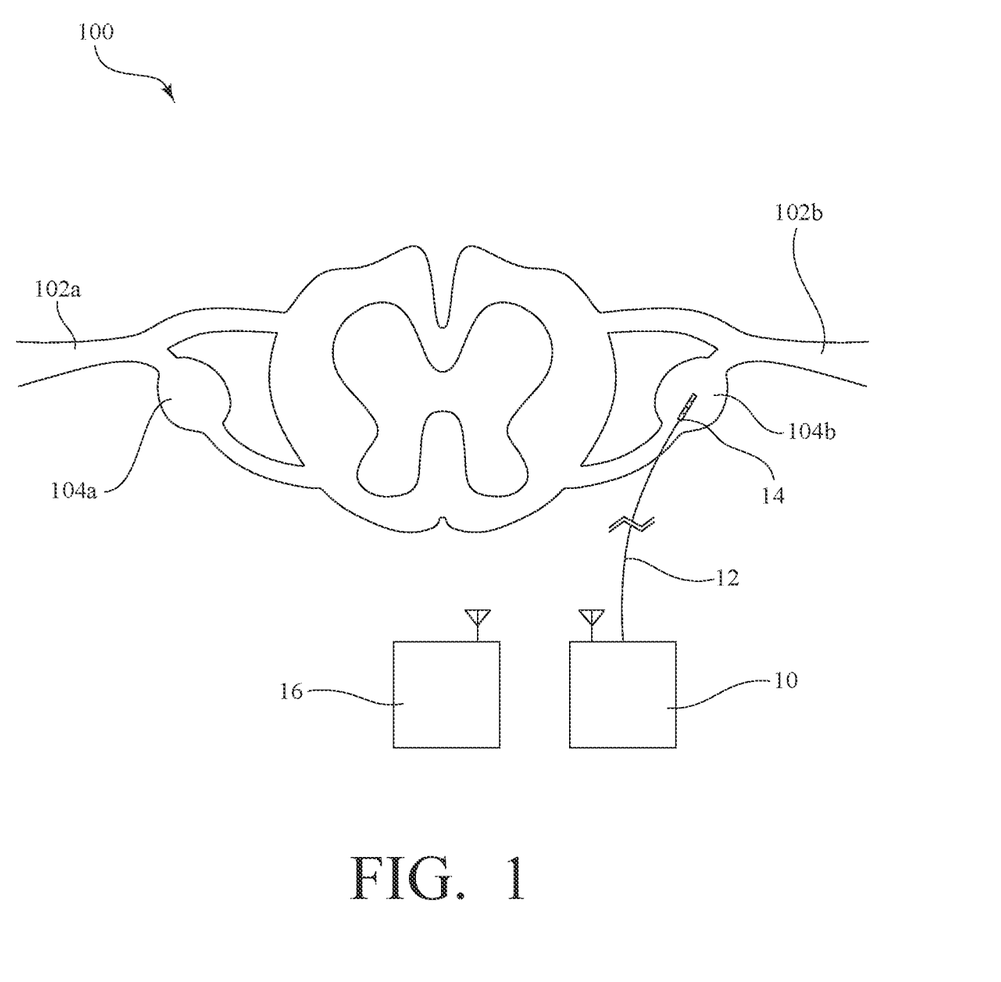
FIG. 1 is a schematic cross-sectional view of a spinal cord.

FIG. 1 is a schematic cross-sectional view of a spinal cord 100, illustrating spinal nerves 102a, 102b extending from the spinal cord 100, including the dorsal root ganglia 104a, 104b. In general, and as shown in FIG. 1, electrical stimulation is provided by an implanted device, which is comprised of a battery-powered generator 10 that is implanted into the body (often under the skin near the buttocks or abdomen), along with one or more thin wires (or leads) 12 that carry electrical energy from the generator 10 to an electrode 14 positioned near the distal end of each lead 12. The distal end of each lead 12 (carrying the electrode 14) is implanted into the dorsal root ganglion 102b. Via an external controller 16, a patient can control the operation of the generator 10, initiating the delivery of electrical energy from the generator 10 to the electrodes 14 and controlling the strength of the stimulation.

One well-known commercially available system for providing DRG stimulation is the Proclaim™ DRG Neurostimulator, which is marketed and sold by Abbott of Austin, Tex.

In traditional spinal cord (SCS) stimulation, it is recommended to anchor the electrodes to the thoracolumbar fascia to prevent lead migration. For example, U.S. Pat. No. 8,311,643, which is also incorporated herein by reference, describes one method and tool for anchoring an electrode so as to prevent migration after implantation.

However, in implanting a system for DRG stimulation, such as the above-identified Proclaim™ DRG Neurostimulator, no such anchoring is recommended. Rather, the leads are provided with loops which are intended to eliminate the need for anchoring. However, there remains a concern that the electrodes will migrate over time, and thus, there is a need for an apparatus and method for anchoring a lead in a system for providing DRG stimulation. However, there are certain challenges unique to anchoring such leads. For example, the diameter and physical characteristics of the leads are different compared to the leads used in an SCS system. For another example, the incision for implanting a DRG system is much smaller (often 1-2 cm) as compared to the incision for implanting a SCS system (often 4-6 cm). In this regard, the larger SCS incision makes visualization and direct access to the thoracolumbar fascia much easier, whereas it is very difficult, if not impossible, to visualize the fascia via the smaller DRG incision.

SUMMARY OF THE INVENTION

The present invention is an apparatus and method for anchoring a lead of a dorsal root ganglion stimulation system.

An exemplary apparatus made in accordance with the present invention generally includes a grommet and a deployment device for positioning and anchoring the grommet to the thoracolumbar fascia, with one or more leads of the dorsal root ganglion stimulation system then secured to the grommet.

The grommet is positioned at a distal end of the deployment device and includes a ring with multiple teeth (or tines) that extend radially inward from the ring. The grommet also carries one or more sutures.

The deployment device includes a plunger that fits in and moves longitudinally relative to a barrel. As such, the plunger can be transitioned between: (i) a stored position, in which the plunger is entirely within the barrel; and (ii) a deployed position, in which the plunger extends beyond a distal end of the barrel. When the plunger of the deployment device is transitioned to the deployed position, the plunger contacts and bends the teeth of the grommet relative to the ring.

In use, the distal end of the barrel of the deployment device is advanced through an incision and into contact with the thoracolumbar fascia. Once so positioned, the plunger is depressed, transitioning it to the deployed position, in which the plunger extends beyond the distal end of the barrel. In the course of this transition, the plunger contacts and bends the teeth of the grommet relative to the ring, extending the teeth outward and into the fascia. The grommet is now anchored to the fascia via the teeth and can be released from the deployment device. Of course, the grommet must be secured to the distal end of the barrel of the deployment device in such a manner that it can be readily released after the grommet has been anchored to the thoracolumbar fascia, as further described below. When the deployment device is withdrawn, the grommet remains anchored to the fascia.

Again, the grommet carries one or more sutures. Once the grommet is anchored to the fascia, the one or more sutures can be tied or otherwise connected to a selected lead of an implanted device, such as a lead of a dorsal root ganglion stimulation system.

As mentioned above, the grommet must be secured to the distal end of the barrel of the deployment device in such a manner that it can be readily released after the grommet has been anchored to the thoracolumbar fascia. In some embodiments, the grommet thus includes one or more upstanding tabs that extend from the ring, and each of the one or more upstanding tabs has a shape that effectively defines a slot. The distal end of the barrel of the deployment device includes a circumferential flange, with notches defined in the circumferential flange. To secure the grommet to the distal end of the barrel of the deployment device, the upstanding tabs of the grommet are aligned with the notches defined in the circumferential flange. The grommet is then advanced (i.e., pushed toward the barrel), such that an upper portion of each of the upstanding tabs is above the circumferential flange. The grommet is then rotated relative to the barrel, such that the upstanding tabs are moved out of alignment with the notches. The engagement of the circumferential flange with the slots defined by the upstanding tabs thus secures the grommet to the deployment device, with the upper portion of each of the upstanding tabs supported by the circumferential flange. Once the grommet is anchored to the thoracolumbar fascia via the teeth, the grommet can be readily released by rotating the deployment device, such that the upstanding tabs of the grommet are again aligned with the notches defined in the circumferential flange. The deployment device can then be withdrawn while the grommet remains anchored to the fascia.

An exemplary method for anchoring a lead of a dorsal root ganglion stimulation system thus includes the steps of: (a) providing a deployment device that includes a plunger that fits in and moves longitudinally relative to a barrel, such that the plunger can be transitioned between (i) a stored position, in which the plunger is entirely within the barrel, and (ii) a deployed position, in which the plunger extends beyond a distal end of the barrel; (b) securing a grommet to the distal end of the barrel of the deployment device, with the grommet carrying one or more sutures, and wherein the grommet includes a ring with multiple teeth that extend radially inward from the ring; (c) inserting the deployment device through an incision and into contact with the thoracolumbar fascia; (d) depressing the plunger of the deployment device, transitioning it to the deployed position, in which the plunger extends beyond the distal end of the barrel of the deployment device, such that the plunger contacts and bends the multiple teeth of the grommet relative to the ring, extending the multiple teeth outward and into the thoracolumbar fascia; (e) releasing the grommet from the deployment device; (f) withdrawing the deployment device; and (g) connecting the one or more sutures carried by the grommet to the lead of the dorsal root ganglion stimulation system.

In some embodiments or implementations, the above-described apparatus and method could also be used in anchoring a lead of a traditional spinal cord (SCS) stimulation system or similar leads or wires implanted in the body.

DETAILED DESCRIPTION OF THE INVENTION

The present invention is an apparatus and method for anchoring a lead of a dorsal root ganglion stimulation system. An exemplary apparatus made in accordance with the present invention generally includes a grommet and a deployment device for positioning and anchoring the grommet to the thoracolumbar fascia, with one or more leads of the dorsal root ganglion stimulation system then secured to the grommet, as further described below.

Figure 2:
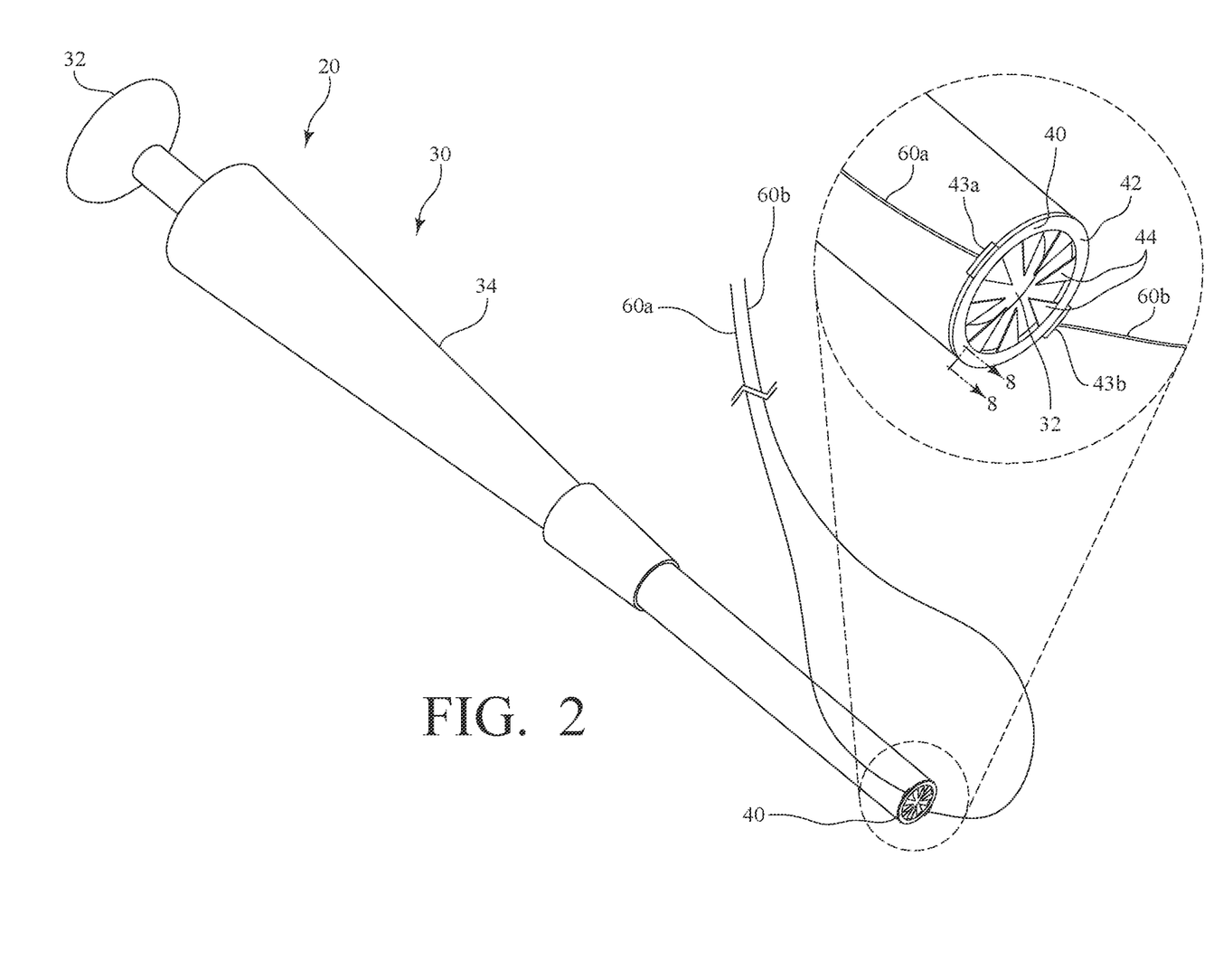
FIG. 2 is a perspective view of an exemplary apparatus made in accordance with the present invention, with the plunger of the deployment device in a stored position.

FIG. 2 is a perspective view of an exemplary apparatus 20 made in accordance with the present invention, which generally comprises a deployment device 30 and a grommet 40 that is positioned at a distal end of the deployment device 30. As also shown in FIG. 2, the deployment device 30 includes a plunger 32 that fits in and moves longitudinally relative to a barrel 34. As such, the plunger 32 can be transitioned between: (i) a stored position, in which the plunger 32 is entirely within the barrel 34; and (ii) a deployed position, in which the plunger 32 extends beyond a distal end of the barrel 34. In FIG. 2, the plunger 32 is in the stored position, entirely within the barrel 34 of the deployment device 30.

Figure 3:
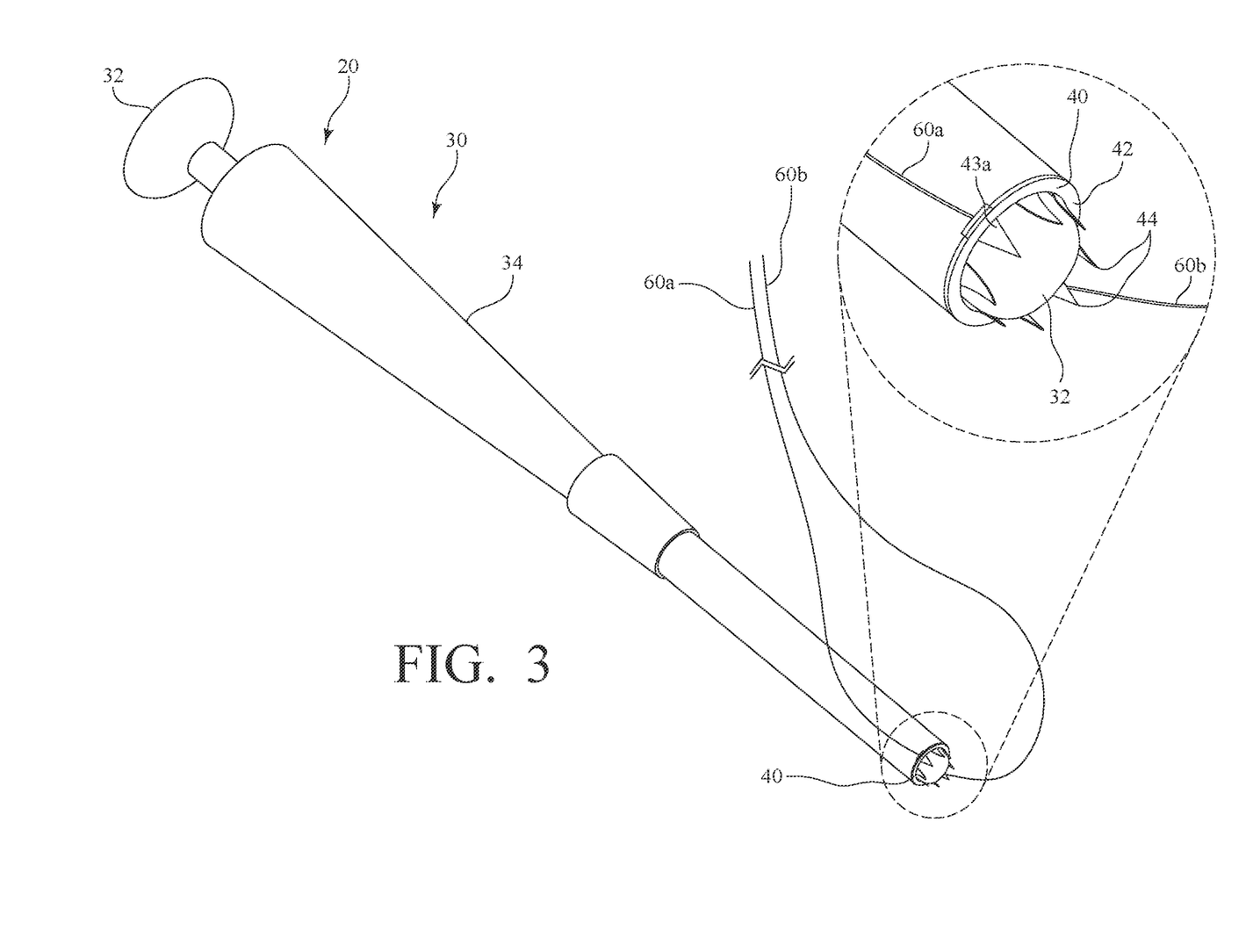
FIG. 3 is a perspective view of the exemplary apparatus similar to FIG. 2, but with the plunger of the deployment device in a deployed position.

FIG. 3 is a perspective view similar to FIG. 2, but with the plunger 32 of the deployment device 30 in the deployed position, extending beyond the distal end of the barrel 34, the importance of which is described below.

Figure 4:
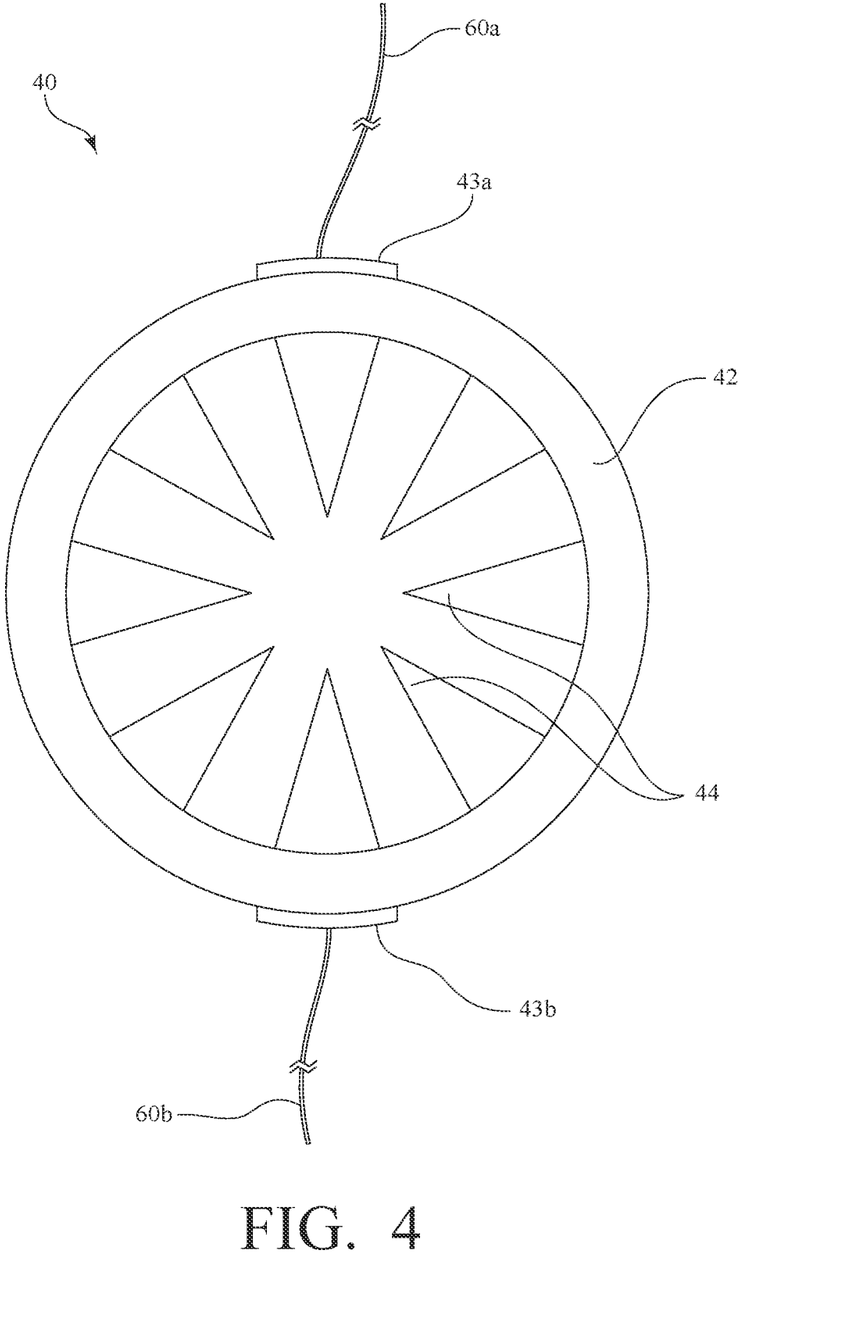
FIG. 4 is a plan view of a grommet of the exemplary apparatus of FIG. 2.

FIG. 4 is a plan view of a grommet 40 of the exemplary apparatus 20. As shown, the grommet 40 is essentially a disk, including a ring 42 with multiple teeth (or tines) 44 that extend radially inward from the ring 42. In this exemplary embodiment, the teeth 44 are illustrated as having a triangular shape; however, various other shapes and configurations of the teeth 44 could be employed without departing from the spirit and scope of the present invention, provided that the teeth 44 allow for the requisite "anchoring" function described below.

Referring again to FIGS. 2 and 3, the grommet 40 is initially secured to the distal end of the barrel 34 of the deployment device 30, as further described below. As shown in FIG. 2, the teeth 44 of the grommet 40 are initially in the same plane, i.e., the grommet 40 is in a substantially flat configuration. However, as shown in FIG. 3, when the plunger 32 of the deployment device 30 is transitioned to the deployed position, the plunger 32 contacts and bends the teeth 44 of the grommet 40 relative to the ring 42, the importance of which is described below. The grommet 40 also carries one or more sutures, the importance of which is also described below. In this exemplary embodiment, and as shown in FIGS. 2 and 3, there are two sutures 60a, 60b that are secured to and each extend from an integral flap 43a, 43b of the ring 42 of the grommet 40.

Figure 5A:
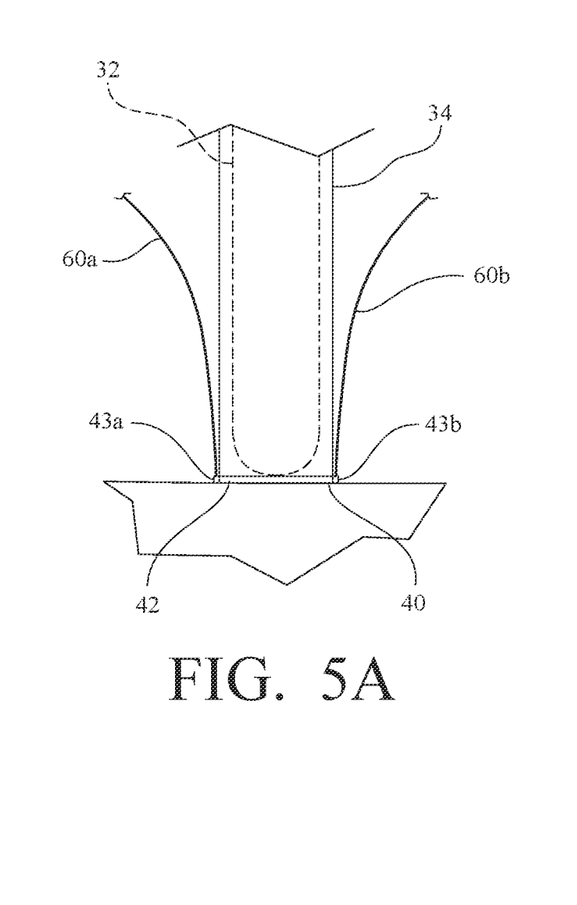
FIGS. 5A-5D are side views of a distal end of the deployment device of the exemplary apparatus of FIGS. 2 and 3, which illustrate the transitioning of the plunger between the stored position and the deployed position, along with withdrawal of the deployment device.
Figure 5B:
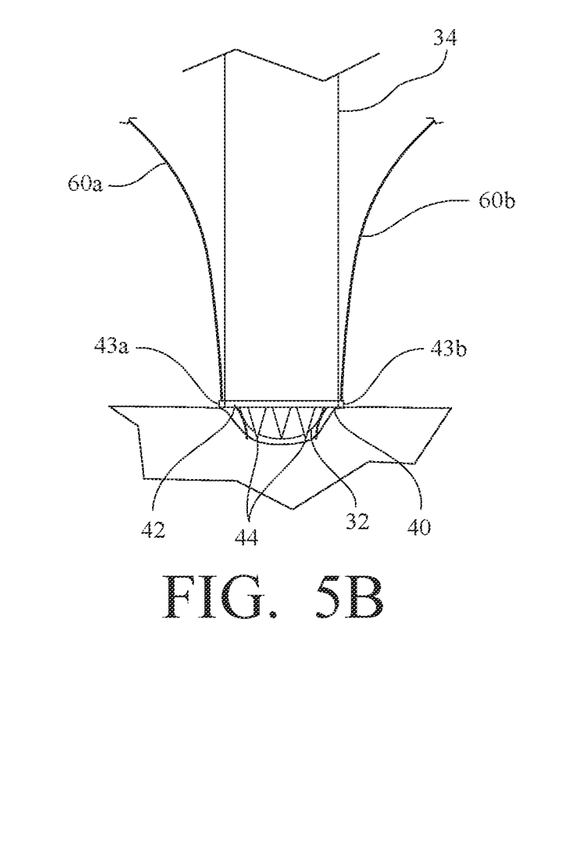
Figure 5C:
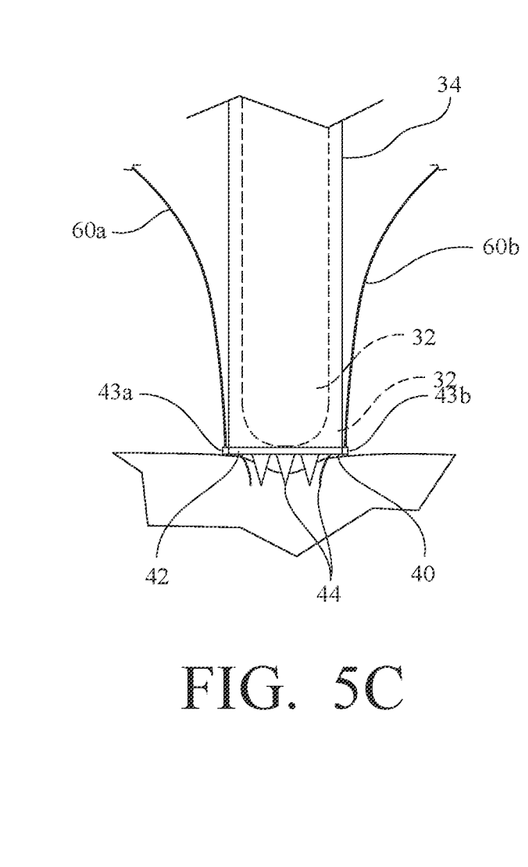
Figure 5D:
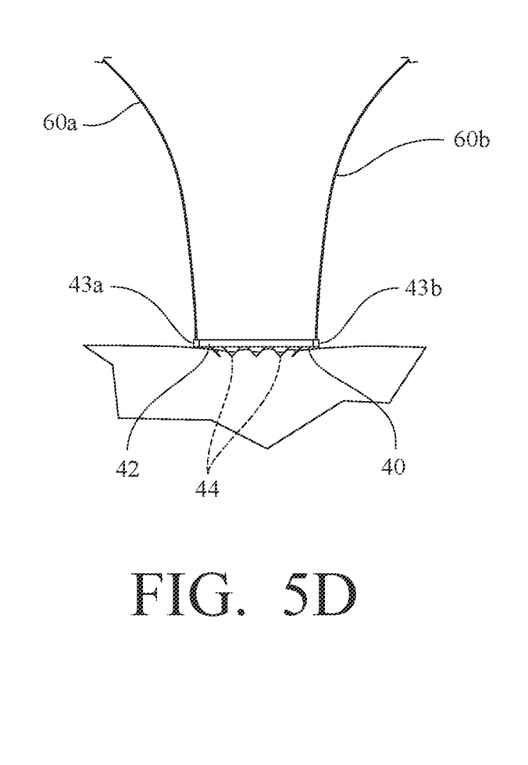

FIGS. 5A-5D are side views of a distal end of the deployment device 30, which illustrate the transitioning of the plunger 32, in use, between (i) the stored position, in which the plunger 32 is entirely within the barrel 34; and (ii) the deployed position, in which the plunger 32 extends beyond a distal end of the barrel 34, along with withdrawal of the deployment device 30. As shown in FIG. 5A, the distal end of the barrel 34 of the deployment device 30 is advanced through an incision and into contact with the thoracolumbar fascia. Once so positioned, the plunger 32 is depressed, transitioning it to the deployed position, in which the plunger 32 extends beyond the distal end of the barrel 34, as shown in FIG. 5B. In the course of this transition, the plunger 32 contacts and bends the teeth 44 of the grommet 40 relative to the ring 42, extending the teeth 44 outward and into the fascia. The grommet 40 is now anchored to the fascia via the teeth 44 and can be released from the deployment device 30, as shown in FIG. 5C. Of course, the grommet 40 must be secured to the distal end of the barrel 34 of the deployment device 30 in such a manner that it can be readily released after the grommet 40 has been anchored to the thoracolumbar fascia, as further described below. Finally, the deployment device 30 is withdrawn, while the grommet 40 remains anchored to the fascia, as shown in FIG. 5D.

As noted above and illustrated in FIGS. 2, 3, 4, and 5A-5D, the grommet 40 carries one or more sutures 60*a*, 60*b*. Once the grommet 40 is anchored to the fascia, the one or more sutures 60*a*, 60*b* can be tied or otherwise connected to the leads 12 of an implanted device, such as that described above with reference to FIG. 1, which is comprised of a battery-powered generator 10 that is implanted into the body (often under the skin near the buttocks or abdomen), along with one or more thin wires (or leads) 12 that carry electrical energy from the generator 10 to an electrode 14 positioned near the distal end of each lead 12. The distal end of each lead 12 (carrying the electrode 14) is implanted into the dorsal root ganglion 102*b*. The one or more sutures 60*a*, 60*b* carried by the grommet 40 can thus be used to anchor a particular lead 12 in place relative to the thoracolumbar fascia.

Figure 1A:
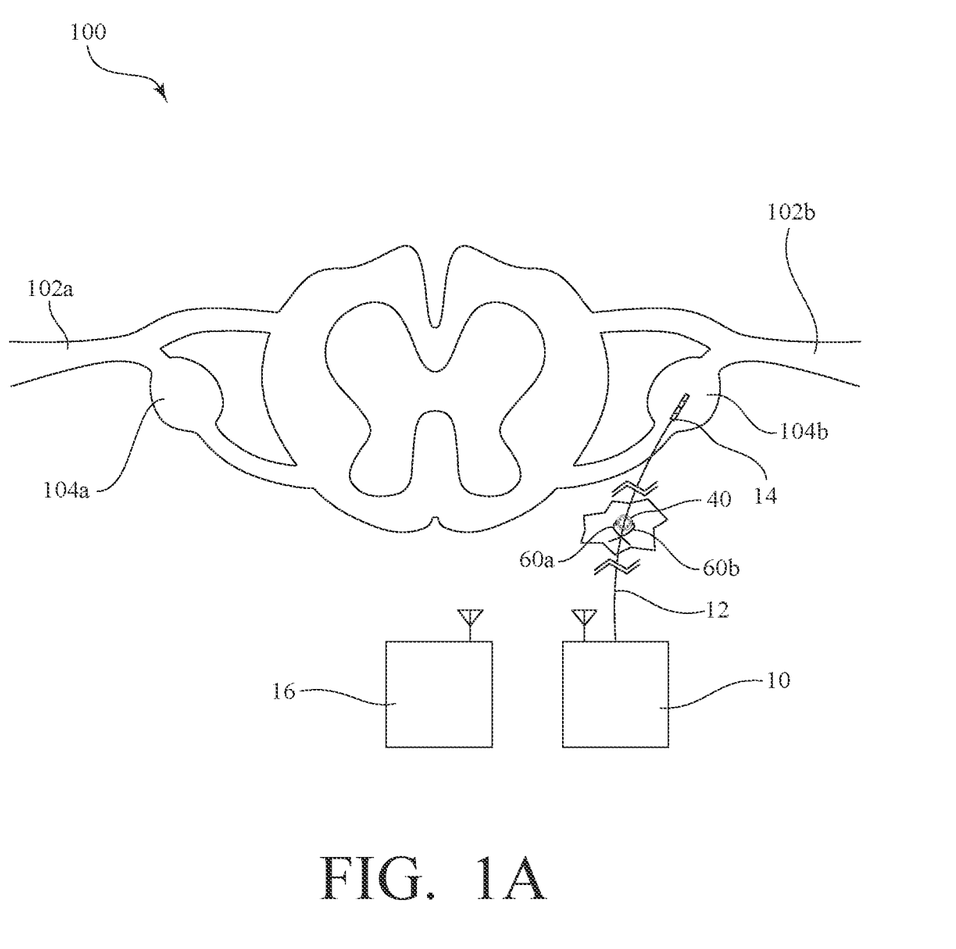
FIG. 1A is a schematic cross-sectional view similar to FIG. 1, but further illustrates the result of the use of an exemplary apparatus and method for anchoring a lead of a dorsal root ganglion stimulation system in accordance with the present invention.

For example, FIG. 1A is substantially identical to FIG. 1, but further illustrates the result of the use of the exemplary apparatus 20. Specifically, through the use of the exemplary apparatus 20 described above, the grommet 40 has been positioned in proximity to the electrode 14 and anchored to the thoracolumbar fascia. The one or more sutures 60*a*, 60*b* are then tied to the lead 12 to anchor the lead 12 in place relative to the thoracolumbar fascia.

As mentioned above, the grommet 40 must be secured to the distal end of the barrel 34 of the deployment device 30 in such a manner that it can be readily released after the grommet 40 has been anchored to the thoracolumbar fascia.

Figure 6:
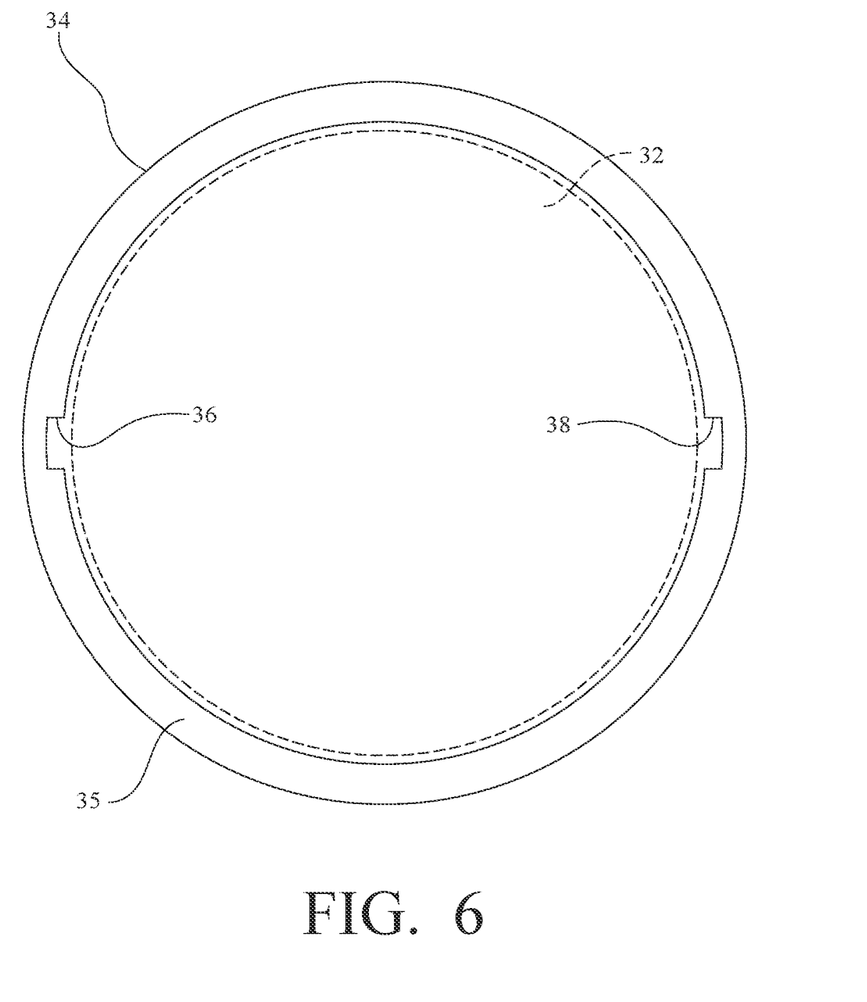
FIG. 6 is a bottom view of the barrel of the deployment device of the exemplary apparatus of FIGS. 2 and 3.

FIG. 6 is a bottom view of the barrel 34 of the deployment device 30.

Figure 7:
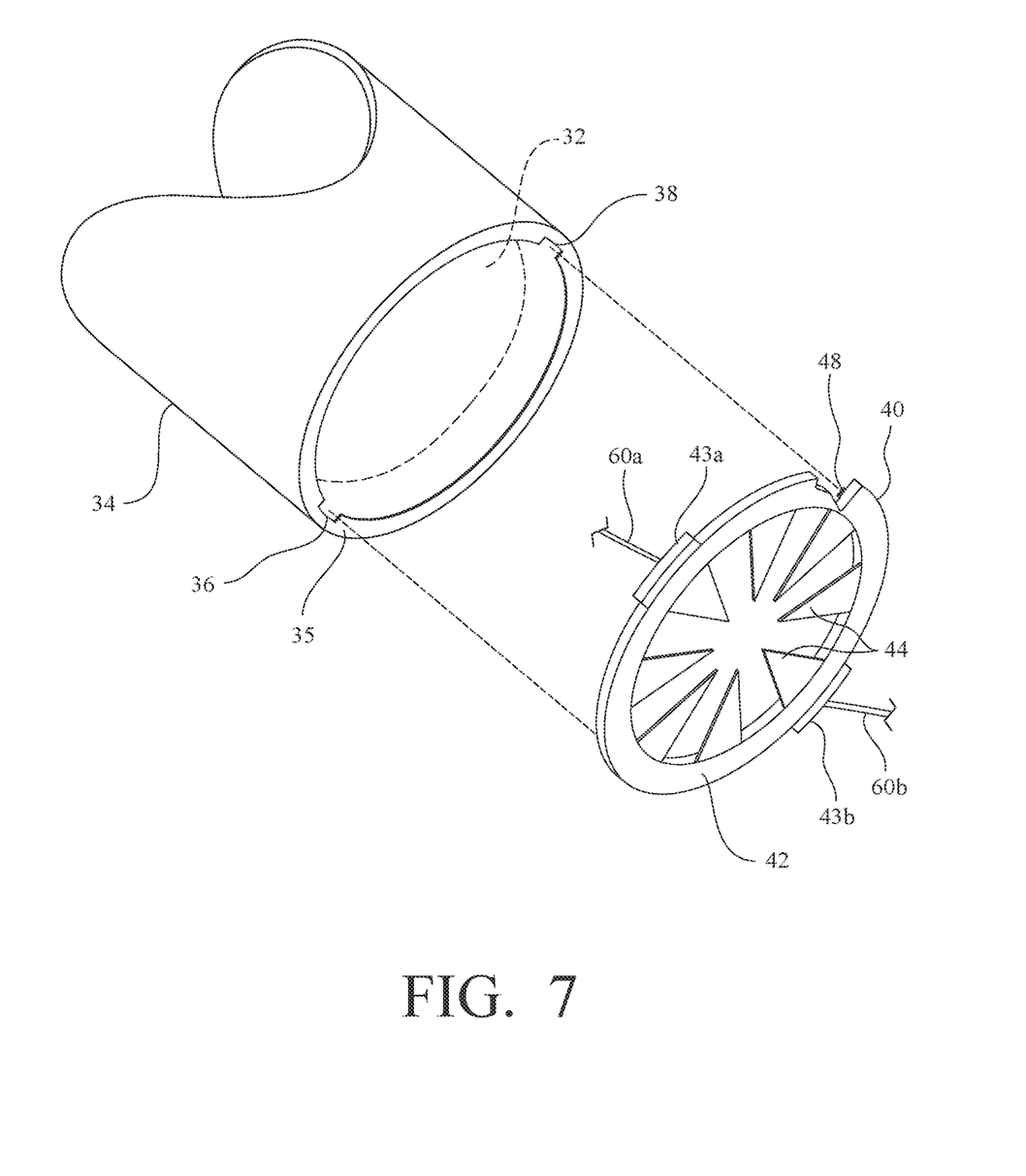
FIG. 7 is an enlarged partial perspective view of the distal end of the barrel of the deployment device of the exemplary apparatus of FIGS. 2 and 3.

FIG. 7 is an enlarged partial perspective view of the distal end of the barrel 34 of the deployment device 30 with the grommet 40 separated from the barrel 34.

Figure 8:
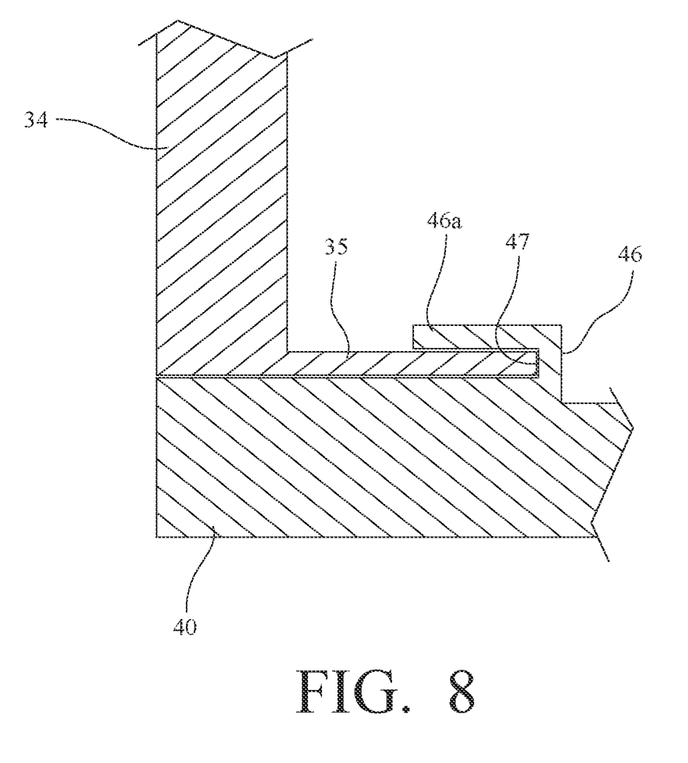
FIG. 8 is a partial sectional view taken along line 8-8 of FIG. 2.

FIG. 8 is a partial sectional view taken along line 8-8 of FIG. 2.

Referring now to FIGS. 6-8, in this exemplary embodiment, the grommet 40 includes one or more upstanding tabs that extend from the ring 42. In this exemplary embodiment, there are two such upstanding tabs 46, 48 that are positioned diametrically opposite one another on the ring 42 of the grommet 40. As best shown in FIG. 8, each upstanding tab 46 (one of which is visible in FIG. 8) has a shape that effectively defines a slot 47. The distal end of the barrel 34 of the deployment device 30 includes a circumferential flange 35. As best shown in FIG. 7, notches 36, 38 are defined in the circumferential flange 35, which, in this exemplary embodiment, are positioned diametrically opposite one another.

Referring still to FIGS. 6-8, to secure the grommet 40 to the distal end of the barrel 34 of the deployment device 30, the two upstanding tabs 46, 48 of the grommet 40 are aligned with the notches 36, 38 defined in the circumferential flange 35. The grommet 40 is then advanced (i.e., pushed toward the barrel 34), such that an upper portion 46*a* (see FIG. 8) of each of the upstanding tabs 46, 48 is above the circumferential flange 35. The grommet 40 is then rotated relative to the barrel 34, such that the upstanding tabs 46, 48 are moved out of alignment with the notches 36, 38. The engagement of the circumferential flange 35 with the slots 47 (see FIG. 8) defined by the upstanding tabs 46, 48 thus secures the grommet 40 to the deployment device 30, with the upper portion 46*a* (see FIG. 8) of each of the upstanding tabs 46, 48 supported by the circumferential flange 35. Once the grommet 40 is anchored to the thoracolumbar fascia via the teeth 44, the grommet 40 can be readily released by rotating the deployment device 30, such that the upstanding tabs 46, 48 of the grommet 40 are again aligned with the notches 36, 38 defined in the circumferential flange 35. The deployment device 30 can then be withdrawn while the grommet 40 remains anchored to the fascia.

Of course, this is only one way in which the grommet 40 can be secured to the distal end of the barrel 34 of the deployment device 30, such that it can be readily released after the grommet 40 has been anchored to the thoracolumbar fascia. Various other means for securing the grommet 40 to the barrel 34 of the deployment device 30 could be employed without departing from the spirit and scope of the present invention.

For example, in an alternative embodiment, the barrel 34 of the deployment device 30 may include an inner wall and an outer wall, with a cavity defined between the inner wall and the outer wall. This cavity would be adapted to receive the upstanding tabs 46, 48 of the grommet 40. In this regard, the distal end of the barrel 34 of the deployment device 30 would include a circumferential ledge extending from the inner wall toward the outer wall, with notches defined in the circumferential ledge. As with the exemplary embodiment described above with respect to FIGS. 6-8, to secure the grommet 40 to the distal end of the barrel 34 of the deployment device 30, the upstanding tabs 46, 48 of the grommet 40 would be aligned with the notches defined in the circumferential flange, the grommet 40 would be advanced (i.e., pushed toward the barrel 34), and then rotated relative to the barrel 34, such that the upstanding tabs 46, 48 are moved out of alignment with the notches. In short, in this alternative embodiment, the means for securing the grommet 40 to the barrel 34 of the deployment device 30 is similar to that described above with respect to FIGS. 6-8, except that the barrel 34 of the deployment device 30 has an inner wall and an outer wall, with a cavity defined between the inner wall and the outer wall in which the upstanding tabs 46, 48 are received.

Figure 9:
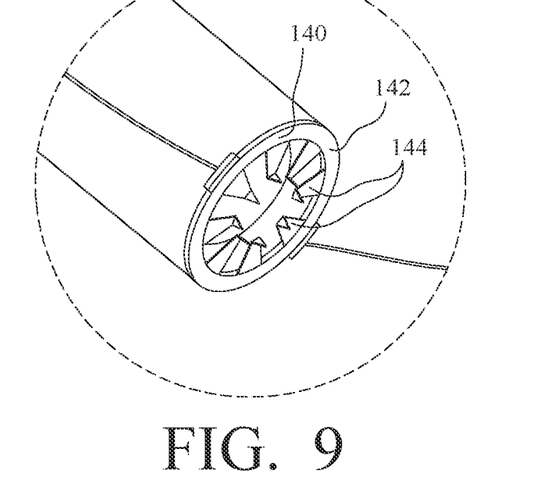
FIG. 9 is an enlarged partial perspective view of an exemplary apparatus made in accordance with the present invention, with the plunger of the deployment device in a stored position, and with an alternate grommet.
Figure 10:
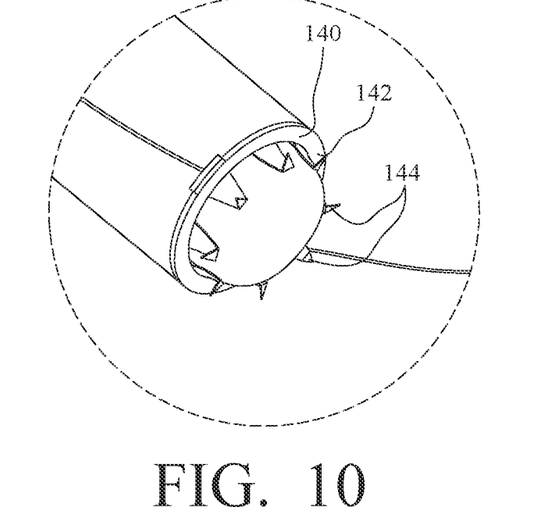
FIG. 10 is an enlarged partial perspective view of the exemplary apparatus similar to FIG. 9, but with the plunger of the deployment device in a deployed position.

In the exemplary embodiment described above, the teeth 44 of the grommet 40 each have a triangular shape and are each substantially flat, as shown, for example, in FIG. 2. However, as noted above, various other shapes and configurations of the teeth 44 could be employed without departing from the spirit and scope of the present invention, provided that the teeth 44 allow for the requisite "anchoring" function. For example, FIGS. 9 and 10 are substantially identical to the enlarged portions of FIGS. 2 and 3 and illustrate the construction of an alternate grommet 140. As shown, the alternate grommet 140 again includes a ring 142 with multiple teeth (or tines) 144 that extend radially inward from the ring 142. Each tooth 144 again has a triangular shape;

however, in this alternative embodiment, there is a 90-degree bend of the tip of each tooth 144, such that, when deployed, the teeth 144 more aggressively engage and grasp the thoracolumbar fascia.

An exemplary method for anchoring a lead of a dorsal root ganglion stimulation system thus includes the steps of: (a) providing a deployment device that includes a plunger that fits in and moves longitudinally relative to a barrel, such that the plunger can be transitioned between (i) a stored position, in which the plunger is entirely within the barrel, and (ii) a deployed position, in which the plunger extends beyond a distal end of the barrel; (b) securing a grommet to the distal end of the barrel of the deployment device, with the grommet carrying one or more sutures, and wherein the grommet includes a ring with multiple teeth that extend radially inward from the ring; (c) inserting the deployment device through an incision and into contact with the thoracolumbar fascia; (d) depressing the plunger of the deployment device, transitioning it to the deployed position, in which the plunger extends beyond the distal end of the barrel of the deployment device, such that the plunger contacts and bends the multiple teeth of the grommet relative to the ring, extending the multiple teeth outward and into the thoracolumbar fascia; (e) releasing the grommet from the deployment device; (f) withdrawing the deployment device; and (g) connecting the one or more sutures carried by the grommet to the lead of the dorsal root ganglion stimulation system.

Finally, although the above description focuses on the use of the apparatus and method of the present invention for anchoring a lead of a dorsal root ganglion stimulation system, it should be recognized that the apparatus and method of the present invention could also be used in anchoring a lead of a traditional spinal cord (SCS) stimulation system or similar leads or wires implanted in the body.

One of ordinary skill in the art will recognize that additional embodiments and implementations are also possible without departing from the teachings of the present invention. This detailed description, and particularly the specific details of the exemplary embodiments and implementations disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. An apparatus for anchoring a lead of a dorsal root ganglion stimulation system, comprising:
    a grommet carrying one or more sutures, wherein the grommet includes a ring with multiple teeth that extend radially inward from the ring; and
    a deployment device configured to receive and secure the grommet at its distal end, wherein the deployment device includes a plunger that fits in and moves longitudinally relative to a barrel, such that the plunger can be transitioned between (i) a stored position, in which the plunger is entirely within the barrel, and (ii) a deployed position, in which the plunger extends beyond a distal end of the barrel;
    wherein, in use, when the plunger of the deployment device is transitioned to the deployed position, the plunger contacts and bends the multiple teeth of the grommet relative to the ring, extending the multiple teeth outward into adjacent fascia, thus anchoring the grommet to the fascia, such that the one or more sutures are available for anchoring a selected lead of the dorsal root ganglion stimulation system to the fascia.

2. The apparatus as recited in claim 1,
    wherein the grommet includes one or more upstanding tabs that extend from the ring;
    wherein the distal end of the barrel of the deployment device includes a circumferential flange, along with one or more notches defined in the circumferential flange; and
    wherein, in use, to secure the grommet to the distal end of the barrel of the deployment device, the one or more upstanding tabs of the grommet are aligned with the one or more notches defined in the circumferential flange, the grommet is then advanced such that an upper portion of each of the one or more upstanding tabs is above the circumferential flange, and the grommet is then rotated, such that the one or more upstanding tabs are moved out of alignment with the one or more notches, with the upper portion of each of the one or more upstanding tabs supported by the circumferential flange.

3. The apparatus as recited in claim 1, wherein the ring of the grommet includes one or more integral flaps, with each of the one or more integral flaps carrying at least one of the one or more sutures.

4. The apparatus as recited in claim 2,
    wherein the grommet includes two upstanding tabs that extend from the ring, with the two upstanding tabs positioned diametrically opposite one another on the ring; and
    wherein two notches are defined in the circumferential flange, with the two notches positioned diametrically opposite one another.

5. An apparatus for anchoring a lead of an electrical stimulation system to fascia within a body, comprising:
    a grommet carrying one or more sutures, wherein the grommet includes a ring with multiple teeth that extend radially inward from the ring;
    a deployment device configured to receive and secure the grommet at its distal end, wherein the deployment device includes a plunger that fits in and moves longitudinally relative to a barrel, such that the plunger can be transitioned between (i) a stored position, in which the plunger is entirely within the barrel, and (ii) a deployed position, in which the plunger extends beyond a distal end of the barrel;
    wherein, in use, when the plunger of the deployment device is transitioned to the deployed position, the plunger contacts and bends the multiple teeth of the grommet relative to the ring, extending the multiple teeth outward into the fascia, thus anchoring the grommet to the fascia; and
    wherein, in use, the one or more sutures are connected to a selected lead of the electrical stimulation system, anchoring the selected lead of the electrical stimulation system to the fascia within the body.

6. The apparatus as recited in claim 5,
    wherein the grommet includes one or more upstanding tabs that extend from the ring;
    wherein the distal end of the barrel of the deployment device includes a circumferential flange, along with one or more notches defined in the circumferential flange; and
    wherein, in use, to secure the grommet to the distal end of the barrel of the deployment device, the one or more upstanding tabs of the grommet are aligned with the one or more notches defined in the circumferential flange, the grommet is then advanced such that an upper portion of each of the one or more upstanding tabs is above the circumferential flange, and the grommet is then rotated, such that the one or more upstanding tabs are moved out of alignment with the one or more notches, with the upper portion of each of the one or more upstanding tabs supported by the circumferential flange.

7. The apparatus as recited in claim 6,
wherein the grommet includes two upstanding tabs that extend from the ring, with the two upstanding tabs positioned diametrically opposite one another on the ring; and
wherein two notches are defined in the circumferential flange, with the two notches positioned diametrically opposite one another.

8. The apparatus as recited in claim 5, wherein the ring of the grommet includes one or more integral flaps, with each of the one or more integral flaps carrying at least one of the one or more sutures.

9. A method for anchoring a lead of a dorsal root ganglion stimulation system, comprising the steps of:
providing a deployment device that includes a plunger that fits in and moves longitudinally relative to a barrel, such that the plunger can be transitioned between (i) a stored position, in which the plunger is entirely within the barrel, and (ii) a deployed position, in which the plunger extends beyond a distal end of the barrel;
securing a grommet to the distal end of the barrel of the deployment device, with the grommet carrying one or more sutures, and wherein the grommet includes a ring with multiple teeth that extend radially inward from the ring;
inserting the deployment device through an incision and into contact with thoracolumbar fascia;
depressing the plunger of the deployment device, transitioning it to the deployed position, in which the plunger extends beyond the distal end of the barrel of the deployment device, such that the plunger contacts and bends the multiple teeth of the grommet relative to the ring, extending the multiple teeth outward and into the thoracolumbar fascia;
releasing the grommet from the deployment device;
withdrawing the deployment device; and
connecting the one or more sutures carried by the grommet to the lead of the dorsal root ganglion stimulation system.

10. The method as recited in claim 9,
wherein the grommet includes one or more upstanding tabs that extend from the ring;
wherein the distal end of the barrel of the deployment device includes a circumferential flange, along with one or more notches defined in the circumferential flange; and
wherein the step of securing the grommet to the distal end of the barrel of the deployment device comprises the substeps of (i) aligning the one or more upstanding tabs of the grommet with the one or more notches defined in the circumferential flange, (ii) advancing the grommet such that an upper portion of each of the one or more upstanding tabs is above the circumferential flange, and (iii) rotating the grommet, such that the one or more upstanding tabs are moved out of alignment with the one or more notches, with the upper portion of each of the one or more upstanding tabs supported by the circumferential flange.

11. The method as recited in claim 10, wherein the step of releasing the grommet from the deployment device comprises the substeps of (i) rotating the deployment device, such that the one or more upstanding tabs of the grommet are aligned with the one or more notches defined in the circumferential flange, and (ii) withdrawing the deployment device while the grommet remains anchored to the thoracolumbar fascia.

* * * * *